United States Patent [19]
Christensen

[11] Patent Number: 6,120,547
[45] Date of Patent: Sep. 19, 2000

[54] ENHANCED PROSTHETIC FOOT STRUCTURE WITH ANKLE REINFORCEMENT

[75] Inventor: Roland J. Christensen, 192 E. 100 North, Fayette, Utah 84630

[73] Assignee: Roland J. Christensen, Fayette, Utah

[21] Appl. No.: 09/188,018

[22] Filed: Nov. 6, 1998

[51] Int. Cl.[7] .................................................... A61F 2/66
[52] U.S. Cl. ................................................ 623/52; 623/38
[58] Field of Search .................................. 623/35, 38, 47, 623/50–52, 53

[56] References Cited

U.S. PATENT DOCUMENTS

| | | |
|---|---|---|
| 1,779,765 | 10/1930 | Eichhorn . |
| 1,996,874 | 4/1935 | Mascau . |
| 2,443,356 | 6/1948 | Mathis . |
| 2,570,735 | 10/1951 | Weise . |
| 2,617,115 | 11/1952 | Ellery . |
| 2,843,853 | 7/1958 | Mauch . |
| 3,906,552 | 9/1975 | Weber ................... 623/38 X |
| 3,956,775 | 5/1976 | Moore . |
| 4,606,332 | 8/1986 | Gibson . |
| 4,865,611 | 9/1989 | Al-Turaiki . |
| 4,938,775 | 7/1990 | Morgan ...................... 623/27 |
| 5,019,109 | 5/1991 | Voisin . |
| 5,030,239 | 7/1991 | Copes . |
| 5,112,356 | 5/1992 | Harris et al. . |
| 5,425,781 | 6/1995 | Allard et al. . |
| 5,458,656 | 10/1995 | Phillips ...................... 623/27 |
| 5,482,513 | 1/1996 | Wilson . |
| 5,509,936 | 4/1996 | Rappoport et al. . |
| 5,728,175 | 3/1998 | Rincoe . |
| 5,769,896 | 6/1998 | Rosendahl et al. . |

FOREIGN PATENT DOCUMENTS

| | | |
|---|---|---|
| 556381 | 11/1958 | Italy .......................... 623/53 |
| 2033772 C1 | 4/1995 | Russian Federation ........ 623/27 |
| 1 550 658 | 8/1979 | United Kingdom ............ 623/38 |

*Primary Examiner*—David H. Willse
*Attorney, Agent, or Firm*—Thorpe, North & Western, LLP

[57] ABSTRACT

A device for joining a prosthetic appendage to a prosthetic limb, comprising rotatable bearings encased within a cylindrical sleeve of resilient material, the cylindrical sleeve having its long axis colinear to the axis of rotation of the bearings. The bearings have a proximal portion affixed to the end of the limb, and a distal portion affixed to the appendage at the point where it is to be joined. The resilient sleeve comprises a top portion which is affixed to the outside surface of the proximal portion of the bearings, a bottom portion which is affixed to the outside surface of the distal portion of the bearings, and a typically bulging central portion which is not affixed to any part of the bearings. When the appendage is rotated relative to the limb about the axis of the bearings, such rotation is resiliently resisted by torsional flexure of the central portion of the resilient sleeve.

32 Claims, 7 Drawing Sheets

ENHANCED PROSTHETIC FOOT STRUCTURE WITH ANKLE REINFORCEMENT

BACKGROUND OF THE INVENTION

1. Field of the Invention

This invention relates to human prosthetic limbs. More particularly, the present invention relates to an improved prosthetic ankle joint which allows resiliently resisted lateral rotation of the foot relative to the ankle, allowing more realistic freedom of motion for a user of the prosthetic device.

2. State of the Art

In recent years, prosthetic devices that more closely imitate real limbs in function and appearance have become more advanced and well known. These more advanced prostheses allow amputees and persons with defects of various kinds to lead more normal lives and participate in sports and recreational activities that they otherwise could not join. For example, many modern prosthetic foot/leg devices, such as those disclosed in U.S. Pat. No. 5,112,356 to Harris et al., U.S. Pat. No. 5,019,109 to Voisin, and U.S. Pat. No. 5,769,896 to Rosendahl et al. incorporate energy storing resilient feet which allow for more natural walking, and even running, jumping, and other athletic movements.

Many known devices also incorporate joints that allow plantar-dorsiflexion and lateral flexion of the foot relative to the leg. However, one common failure of many known prosthetic joints is that they do not allow for lateral rotation of the foot relative to the ankle. Of the known devices that do allow lateral rotation, many unnaturally constrain the rotation, such as in U.S. Pat. No. 3,956,775 to Moore, or allow rotation only in discrete increments, such as U.S. Pat. No. 4,865,611 to Al-Turaiki, or allow it in an unnatural manner, such as in U.S. Pat. Nos. 5,019,109 to Voisin and U.S. Pat. No. 5,030,239 to Copes. Such lateral rotation is desirable for athletic activities such as golf, basketball, and other sports where lateral rotation of the foot relative to the ankle is desirable. Moreover, resilient resistance to such rotation is desirable to approximate the function of the human ankle.

OBJECTS AND SUMMARY OF THE INVENTION

It is therefore an object of the present invention to provide a prosthetic ankle joint that allows lateral rotation of the ankle where the rotation is not constrained within some arbitrary range.

It is another object of this invention to provide a prosthetic ankle joint wherein lateral rotation is resiliently resisted in a manner similar to that of the natural human ankle joint.

It is another object of this invention to provide a prosthetic ankle joint wherein lateral rotation is resisted by torsional resisting forces that increase in magnitude in proportion to the angle of lateral rotation.

It is yet another object of this invention to provide a prosthetic ankle joint wherein resistance to lateral rotation is selectively adjustable by the user.

The above and other objects are realized in an apparatus for joining a prosthetic appendage to a prosthetic limb, comprising rotatable bearing means disposed between and affixed to the end of an artificial limb, such as a leg, and the connection point of an artificial appendage such as a foot so as to allow rotation of the appendage about the long axis of the limb. A cylindrical sleeve of resilient polymer material, such as polyethylene, with or without fiber reinforcement, encases the rotatable bearing means with its long axis colinear to the axis of rotation of the bearing means, and the inside surface of the sleeve is affixed to the top and bottom portions of the rotatable bearing means, with the central portion of the cylinder of resilient material not affixed to the bearing means, such that when the appendage is transversely rotated relative to the limb, such rotation is resiliently resisted by torsional flexure of the central portion of the sleeve.

In an alternative embodiment, the central portion of the sleeve further comprises a bulge around its circumference and directed away from the rotatable bearing means, such that there is provided a larger amount of resilient material that is not affixed, thus allowing greater freedom of rotation.

In yet another alternative embodiment, the central portion of the sleeve further comprises slots extending from the outside surface to the inside surface of the sleeve, whereby the resistance of the sleeve to torsional flexure is reduced.

In yet another alternative embodiment, the central portion of the sleeve comprises slits extending from the outside surface to the inside surface of the sleeve, or only partially therethrough, whereby the resistance of the sleeve to torsional flexure is reduced by a desired amount.

Other objects and features of the present invention will be apparent to those skilled in the art, based on the following description, taken in combination with the accompanying drawings.

DETAILED DESCRIPTION OF THE PREFERRED EMBODIMENT

Figure 1:
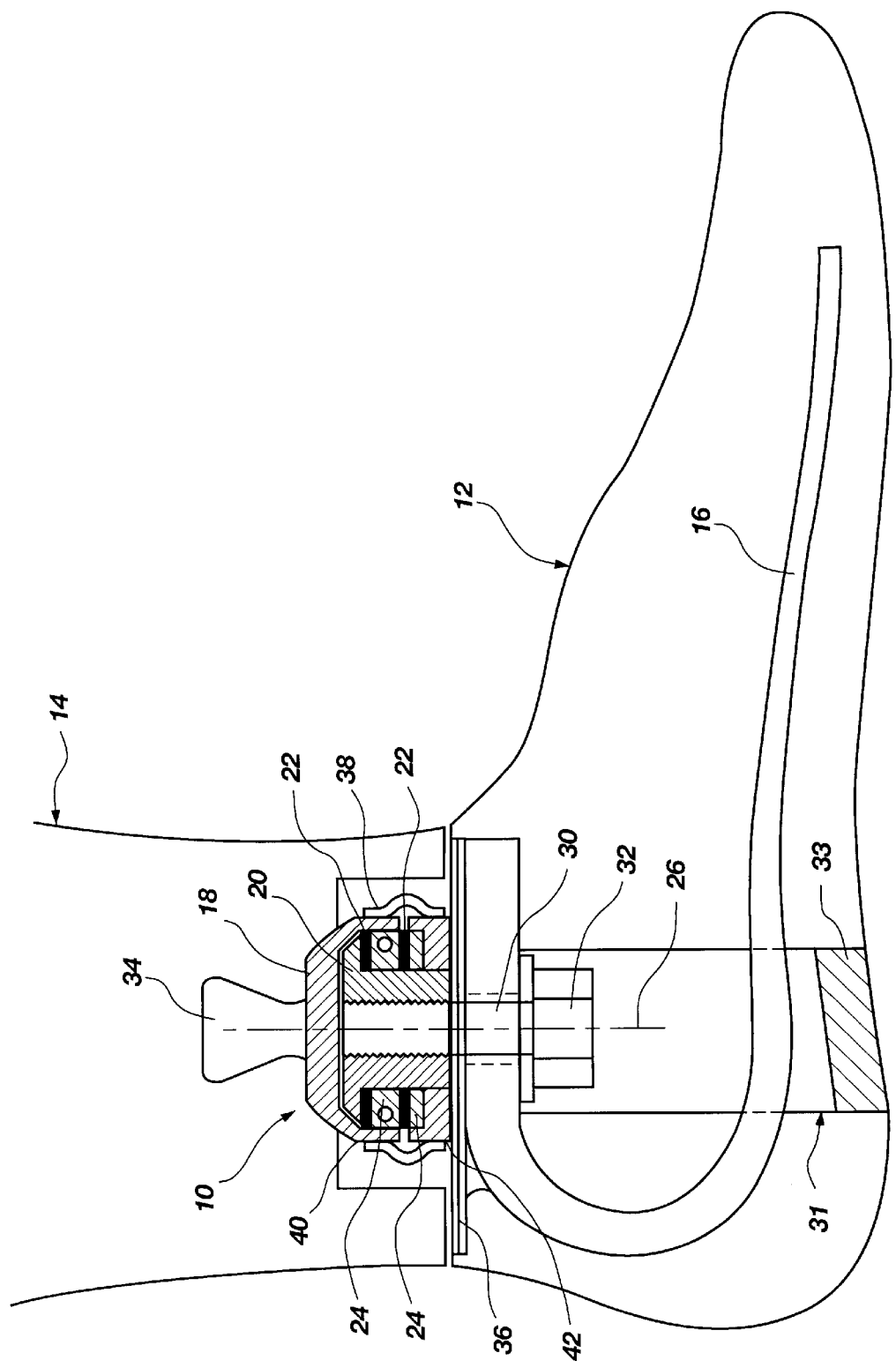
FIG. 1 provides a cross-sectional view of the prosthetic joint of the present invention installed as it would be used to join a prosthetic foot to a prosthetic leg.
Figure 2:
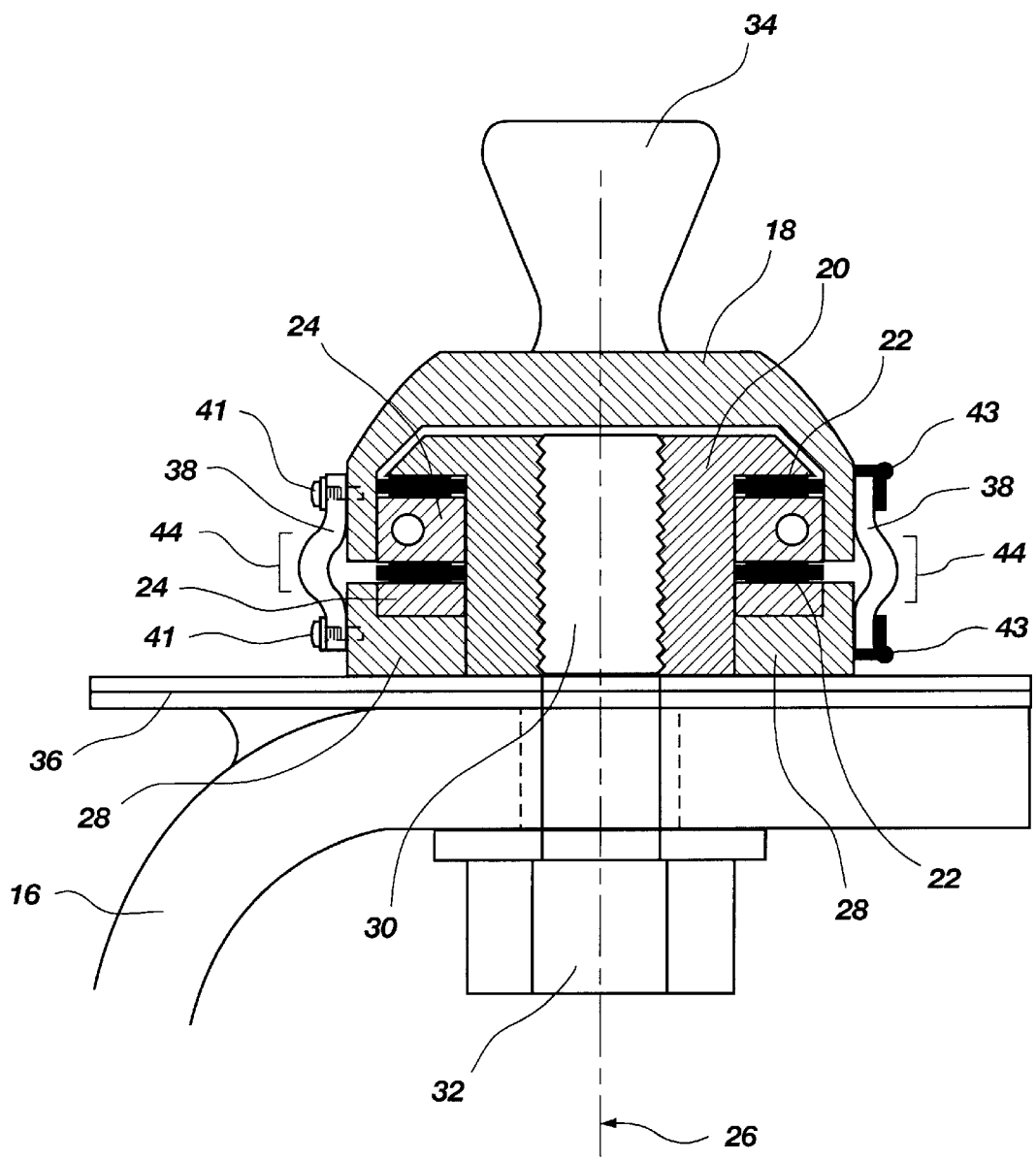
FIG. 2 provides a close-up cross-sectional view of the prosthetic joint of FIG. 1.

Referring now to the drawings:

FIG. 1 provides a cross-sectional view of the prosthetic joint of the present invention as it would be used to join a prosthetic foot to a prosthetic leg, and FIG. 2 provides a close-up view of this joint. The joint, shown generally at 10, is installed as it would be used to join a prosthetic foot 12, having a resilient, energy-storing keel 16, to a prosthetic leg 14. The leg and foot may be of any construction known in the art, such as rigid foam or other durable, lightweight materials, and may comprise a flexible polyurethane skin or other aesthetically desirable configuration. The energy-storing keel 16 is well known in the art, and such devices are now commonly used for running and other athletic activities. It will be appreciated that the joint 10 as disclosed herein may be used to join parts of prosthetic limbs of other configurations such as prosthetic hands to arms, etc.

The joint 10 is generally comprised of an upper housing 18 and a central core 20. The upper housing and core are connected by bearing means 22, such as needle bearings, and resilient pads 24 which allow the housing and core to be freely rotatable with respect to each other about a vertical axis of rotation 26. It will be appreciated that the core 20, housing 18, bearings 22 and pads 24 will preferably be cylindrical in shape and coaxially joined so as to allow axial rotation. As depicted in FIG. 2, there is also an annular ring 28 which joins the outside of the lower portion of the core 20, and supports the pads 24 and bearings 22. It will be appreciated that this ring could be integrally formed as part of the core 20 if it is so desired.

The joint 10 is connected to the foot 12 via a bolt 30 which engages the keel 16 with bolt head 32 and extends into the center of the core 20. As shown in FIG. 1 and FIG. 2, the bolt 30 threadably engages the core 20 so as to securely attach the joint 10 to the foot 12. It will be appreciated that other means may be employed to securely attach the joint to the foot yet prevent rotation of the core 20 and ring 28 relative to the foot 12. As depicted in FIG. 1, the foot 12 is advantageously provided with a cylindrical opening 31 which surrounds the bolt head 32 and extends from the bolt head to the bottom of the foot. This opening allows easy access to the bolt head by, for example, a socket wrench for quickly and easily disconnecting the foot 12 from the ankle 14 when needed for maintenance or to change the sleeve 38, as will be discussed below. The bottom of the opening 31 may be plugged with a plug 33 as shown for aesthetic purposes and to provide a desirably large bearing surface on the bottom of the foot 12.

The foot structure includes a flat top plate 36 to facilitate secure attachment of the core 20 and ring 28 to the top of the foot keel, which has a partly curved upper surface. At the upper end, the housing 18 is attached to the leg 14 by means of an attachment part 34, such as an inverted pyramid or knob, atop the center of the housing. This knob is axially aligned with the bolt 30, and engages the material of the leg in such a way as to prevent rotation of the housing relative to the leg.

With the joint as heretofore described, the foot may freely rotate about axis 26 in a full circle. However, to provide resilient resistance to this rotation, the joint 10 is provided with a resilient cylindrical sleeve 38 which surrounds and engages the outside of the joint 10. This sleeve is made of a suitably resilient polymer material such as polyurethane or fiber reinforced polyurethane. It will be appreciated that other similar materials may also be suitably employed, with or without fiber reinforcement. The upper end of the sleeve 38 is attached to the outside of the housing 18 in the location designated at 40. The sleeve is preferably attached by means of compatible adhesives such as urethane adhesive, but it will be appreciated that other attachment means may be used as described below. The lower end of the sleeve 38 is also attached to the outside of the ring 28 in the location designated at 42 in a similar manner.

With the sleeve 38 fixedly attached to the housing and the ring, there is provided resilient resistance to rotation of the foot relative to the ankle. When the foot 16 is rotated about axis 26, the core 20 and ring 28, which are securely attached thereto, rotate with it. However, bearing means 22 allow the housing 18 and ankle 14 to remain unrotated. However, the torsional strength of the sleeve 38 resists this rotation, and will bring the foot back into its normal position when the rotational force is released. The magnitude of the resistance to rotation depends on the strength and thickness of the material which comprises the sleeve 38. A suitable sleeve comprised of polyurethane will preferably be in the range of 1/16" to 1/4" thick to provide adequate torsional resistance.

In alternative embodiments of the present invention, other means may be provided to attach the sleeve 38 to the housing 18 and ring 28 such as mechanical attachments. For example, the sleeve 38 may be attached by means of a plurality of screws 41 which are affixed circumferentially around the outside of the housing 18, as shown in FIG. 2. Alternatively, the sleeve 38 may be affixed around the outside of the housing 18 by means of a plurality of spring biased clips 43, also shown in FIG. 2, which firmly grip the top and bottom of the sleeve. It will be apparent to those skilled in the art that other attachment means may be provided which will satisfy the objects of the present invention. These various attachment configurations will allow selective reinstallation of various sleeves 38 which provide differing levels of resistance to rotation for different uses. For example, if a user desires to play basketball, a thicker or stiffer sleeve may be desired than for running or golf, or walking.

In the preferred embodiment of the present invention, the central area of the sleeve, designated at 44, comprises an annular bulge. This bulge provides additional material between the upper location of attachment 40 to the housing, and the lower location of attachment 42 to the ring. It will be appreciated that this bulge provides additional unfixed sleeve material between the locations of affixation, and allows reduced torsional resistance for a given thickness and material of the sleeve.

Figure 3:
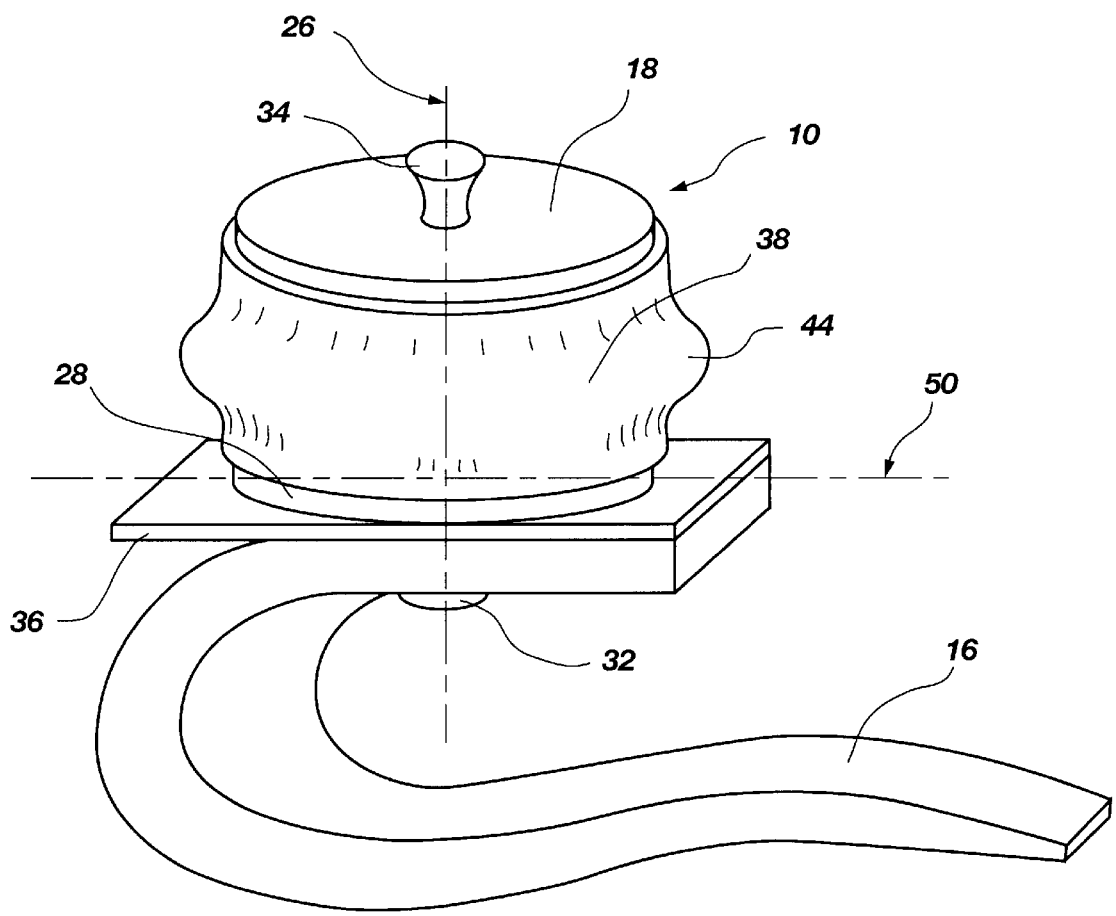
FIG. 3 shows a pictorial view of the prosthetic joint of the present invention connected to an energy-storing foot structure in its natural, un-deflected configuration.
Figure 4:
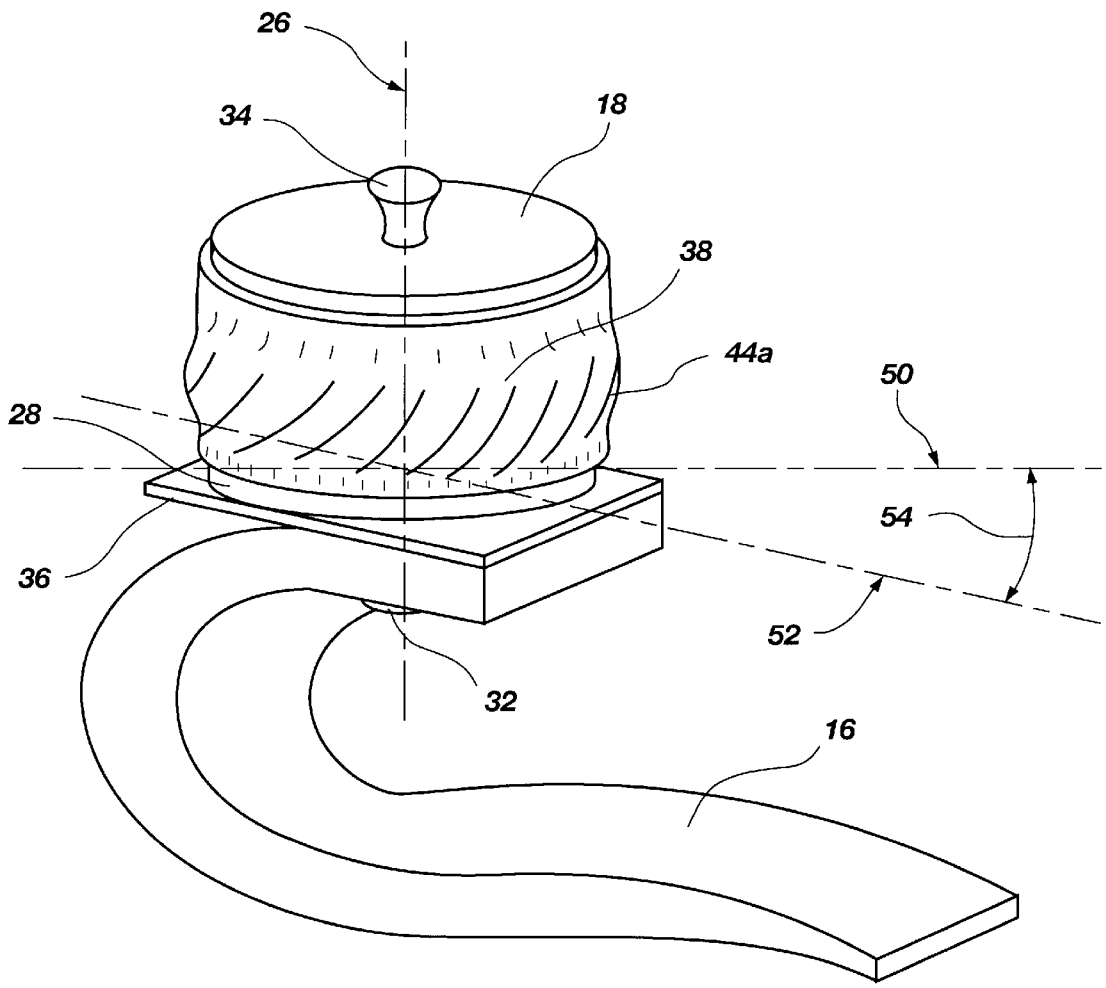
FIG. 4 shows a pictorial view of the prosthetic joint of the present invention connected to a laterally deflected energy-storing foot structure.

Turning to FIG. 3, there is shown a pictorial view of the prosthetic joint of the present invention connected to an energy-storing foot structure in its natural, un-deflected configuration. In this configuration, the forward axis 50 of the joint, intended to represent the forward walking direction, is aligned with the long axis of the foot 16, and the sleeve 38 is not stressed. FIG. 4, however, shows the foot 16 laterally deflected such that the long axis 52 of the foot is deflected from the forward axis 50 of the joint by some angle 54. This rotational deflection creates a torsional stress in the sleeve 38, deforming the bulge 44 into some deformed bulge 44a. In this situation the torsional elasticity of the sleeve 38 resists the rotation, and tends to rotate the foot back into its natural undeflected configuration. It is this function of the present invention which provides its primary utility. For example, a user of this device would have greater mobility when playing basketball, for example, by being able to plant the foot firmly on the ground and still rotate the leg somewhat, as can be done by ordinary human legs.

Figure 5:
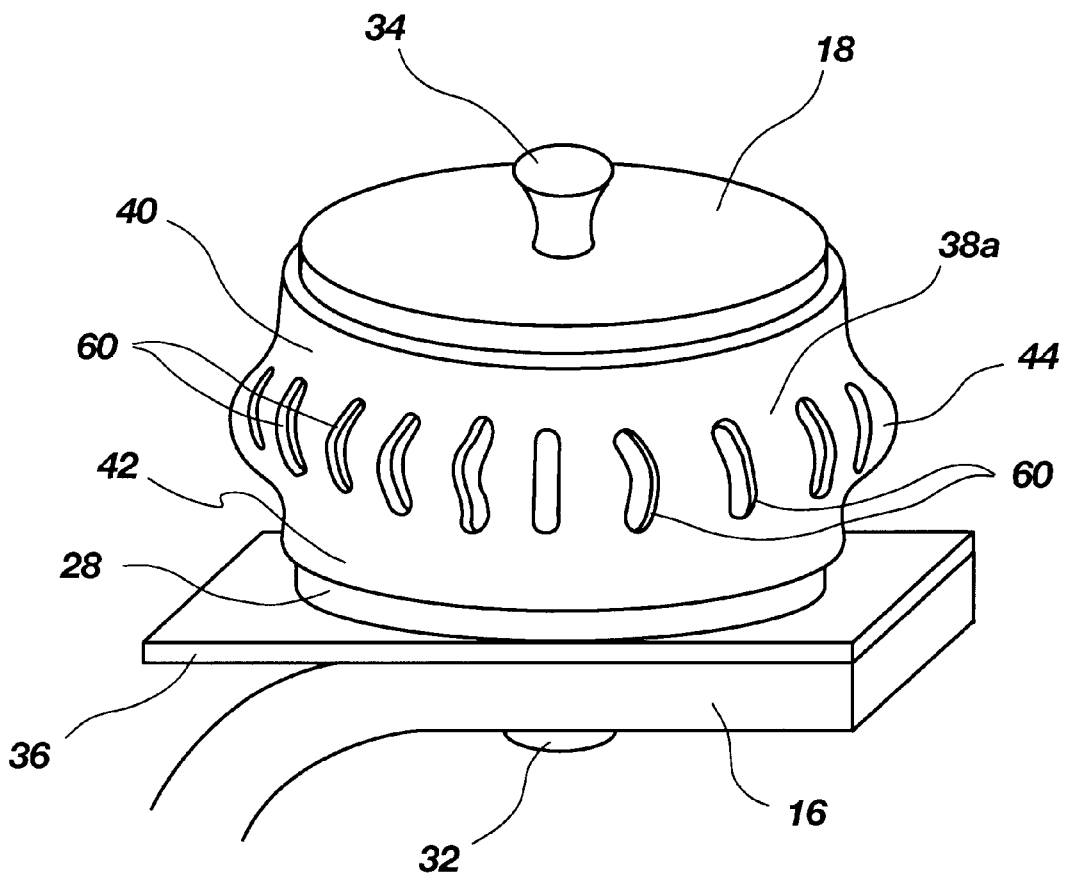
FIG. 5 shows a pictorial view of the prosthetic joint of the present invention in which the resilient sleeve includes full-depth vertical slots.
Figure 7A:
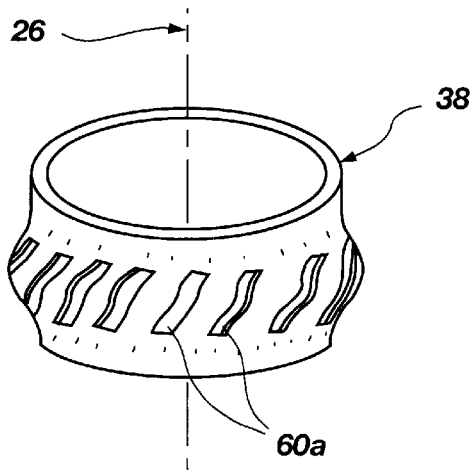
FIG. 7A depicts an alternative embodiment of the resilient sleeve of FIG. 5 wherein the slots are slanted.
Figure 7B:
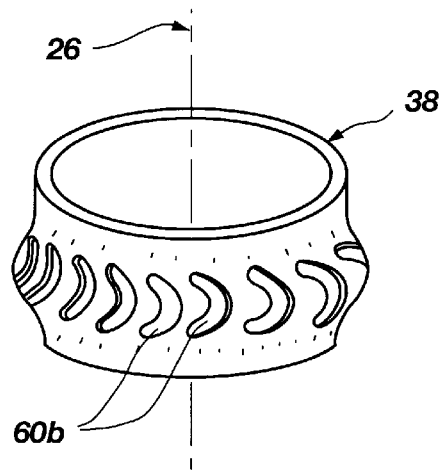
FIG. 7B depicts an alternative embodiment of the resilient sleeve of FIG. 5 wherein the slots are curved.

FIG. 5 shows a pictorial view of an alternative embodiment of the sleeve 38 of the present invention. In this embodiment the resilient sleeve 38 is provided with a plurality of vertically oriented slots 60 located about the middle, bulged region 44 of the sleeve. Alternatively, as shown in FIG. 7A, the sleeve may be provided with slots 60a that are oriented in a slanted configuration relative to the vertical axis 26. Alternatively again, as shown in FIG. 7B, the sleeve may be provided with slots 60b that are curved relative to the vertical axis 26. It will be apparent that the slots 60*b* may be curved in any desired configuration such as having a single curvature as shown in FIG. 7B, or having double curvature as shown with the curved slits 61*b* in FIG. 7D, described below, or any other desired configuration. As noted above with regard to the bulge 44, the slots 60, 60*a*, or 60*b* likewise reduce the torsional resistance of the sleeve for a given thickness and choice of material, the magnitude of the reduction depending in part on the configuration of the slots. Normally these slots will not extend into the upper and lower regions of affixation, 40 and 42, so as not to compromise the strength of affixation of the sleeve to the housing 18 and the ring 28.

Figure 6:
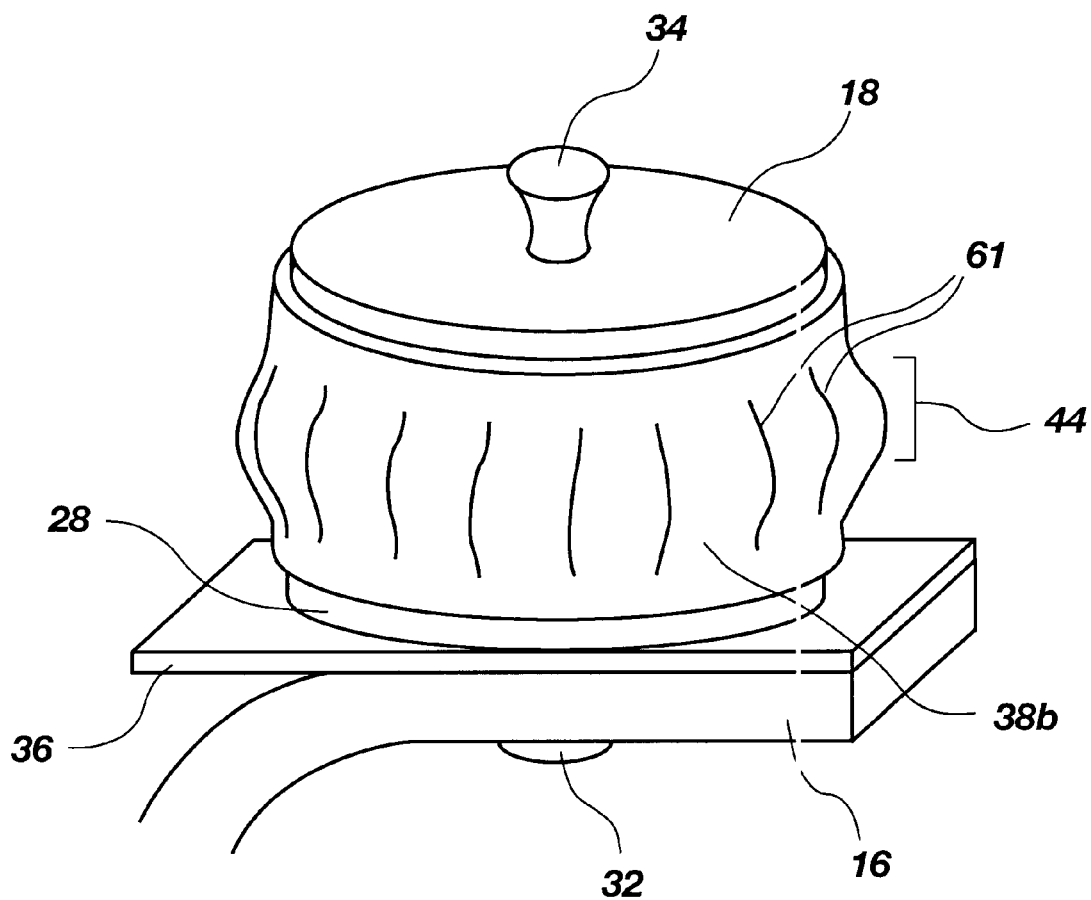
FIG. 6 shows a pictorial view of the prosthetic joint of the present invention in which the resilient sleeve includes full or partial depth slits in its side.
Figure 7C:
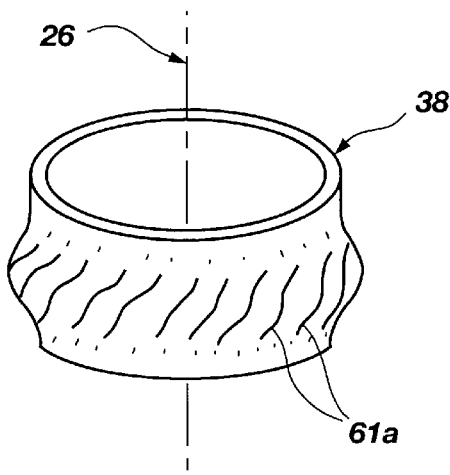
FIG. 7C depicts an alternative embodiment of the resilient sleeve of FIG. 6 wherein the slits are slanted.
Figure 7D:
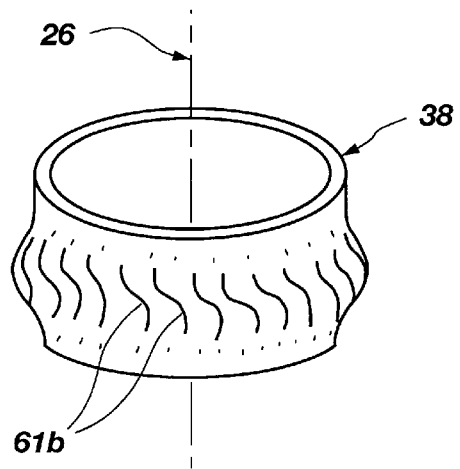
FIG. 7D depicts an alternative embodiment of the resilient sleeve of FIG. 6 wherein the slits are curved.

As an alternative to the slots of FIGS. 5, 7A, and 7B, a resilient sleeve 38*b* having vertical slits 61 in its side may be provided as shown in FIG. 6. Alternatively, as shown in FIG. 7C, the sleeve may be provided with slits 61 a that are oriented in a slanted configuration relative to the vertical axis 26, or as shown in FIG. 7B, the slits 61*b* may be curved relative to the vertical axis 15 26. As noted above with respect to the slots, the curved slits 61*b* may also be curved in any desired configuration such as having double curvature as shown in FIG. 7D, or having single curvature like the slots shown in FIG. 7B, or any other desired configuration. The slits may penetrate through the full thickness of the sleeve 38*b*, or may be partial depth, depending on the desired torsional stiffness of the sleeve.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A device configured for joining a prosthetic appendage to a prosthetic limb, comprising:

rotatable bearing means having a proximal portion and a distal portion, said proximal portion being configured to be affixed to an end of a prosthetic limb, and said distal portion being configured to be affixed to said appendage, the proximal and distal portions being limited to rotational motion with respect to one another about an axis of rotation;

a generally cylindrical sleeve of resilient material having a top portion, a bottom portion, a central portion, an inside surface, and an outside surface, said sleeve oriented so as to surround the bearing means with a long axis colinear to the axis of rotation of the bearing means, the inside surface of the top portion of the sleeve being affixed to the proximal portion of the rotatable bearing means, the inside surface of the bottom portion of the sleeve being affixed to the distal portion of the rotatable bearing means, such that when the proximal and distal portions of the bearing means are rotated relative to each other, such rotation is resiliently resisted by torsional flexure of the central portion of the sleeve; and a bulge, formed around the circumference of the sleeve and directed away from the rotatable bearing means, to provide additional unfixed sleeve material to reduce the magnitude of torsional resistance provided by the central portion of the sleeve.

2. The apparatus as described in claim 1 further comprising stress relief means formed in the central portion of the sleeve, said stress relief means extending at least partially between the outside surface and the inside surface of the sleeve, and configured to reduce the resistance of the sleeve to torsional flexure.

3. The apparatus as described in claim 2 wherein the stress relief means is selected from the group comprising a plurality of slots and a plurality of slits formed in the sleeve.

4. The apparatus as described in claim 3 wherein the stress relief means are oriented parallel to the central axis of the cylindrical sleeve.

5. The apparatus as described in claim 3 wherein the stress relief means extends from the outside surface to the inside surface of the sleeve.

6. The apparatus as described in claim 1 wherein the cylindrical sleeve is formed of materials selected from the group consisting of polyethylene, polypropylene, polyurethane, polyvinyl, urethane, rubber, and fiber reinforced composites of the foregoing polymers.

7. The apparatus as described in claim 6 wherein the material is in the range of $\frac{1}{16}$ in. to $\frac{1}{4}$ in. thick.

8. The apparatus as described in claim 6 wherein the ratio of the length of the sleeve measured along its central axis to the thickness of the material is in the range of 4:1 to 16:1.

9. The apparatus as described in claim 1 wherein the sleeve is affixed to the rotatable bearing means by means of an adhesive.

10. The apparatus as described in claim 1 wherein the sleeve is affixed to the rotatable bearing means by mechanical connection means.

11. The apparatus as described in claim 10 wherein the mechanical connection means is selectively releasable by a user of the apparatus such that a user may remove and replace sleeves at will, so as to allow selective installation of sleeves of varying resistance.

12. The device as described in claim 1, wherein the bearing means includes a plurality of rotating bearings.

13. The device as described in claim 1, wherein the sleeve and bearing means are configured to retain the bulge formed in the sleeve while the appendage is in a natural, undeflected configuration.

14. A device configured for joining a prosthetic appendage to a prosthetic limb, comprising:

a cylindrical proximal connector means having a top, a bottom, and an outside surface, the top of said connector means being configured to be affixed to said limb;

a cylindrical distal connector means having a top, a bottom, and an outside surface, the bottom of said connector means being configured to be affixed to said prosthetic appendage;

rotatable bearing means disposed between and rotatably joining the bottom of said proximal connector means to the top of said distal connector means configured to allow rotation of the proximal and distal connector means relative to each other about an axis of rotation substantially parallel to a long axis of said limb;

a generally cylindrical sleeve of resilient material having a top portion, a bottom portion, a central portion, an inside surface, and an outside surface, said sleeve oriented so as to surround the proximal connector means, the bearing means, and the distal connector means, with a long axis of said sleeve colinear with said axis of rotation, the inside surface of the top portion of the sleeve being affixed to the outside surface of the proximal connector means, the inside surface of the bottom portion of the sleeve being affixed to the outside surface of the distal connector means, and the central portion of said sleeve further comprising a bulge around the circumference thereof, said bulge directed away from the axis of the rotatable bearing means, such that when the proximal and distal connector means are rotated relative to each other, such rotation is resiliently resisted by torsional flexure of the bulged central portion of the sleeve.

15. The invention as described in claim 14 further comprising stress relief means formed in the central portion of the sleeve, said stress relief means extending at least partially between the outside surface and the inside surface of the sleeve, and configured to reduce the resistance of the sleeve to torsional flexure.

16. The apparatus as described in claim 15 wherein the stress relief means is selected from the group comprising a plurality of slots and a plurality of slits formed in the sleeve.

17. The apparatus as described in claim 16 wherein the stress relief means are oriented parallel to the central axis of the cylindrical sleeve.

18. The apparatus as described in claim 16 wherein the stress relief means extends from the outside surface to the inside surface of the sleeve.

19. The invention as described in claim 14 wherein the cylindrical sleeve is formed of materials selected from the group consisting of polyethylene, polypropylene, polyurethane, polyvinyl, urethane, rubber, and fiber reinforced composites of the foregoing polymers.

20. The invention as described in claim 19 wherein the material is in the range of ⅟₁₆ in. to ¼ in. thick, and has a durometer hardness of 45 to 90 shore A.

21. The invention as described in claim 19 wherein the ratio of the length of the sleeve measured along its central axis to the thickness of the material is in the range of 4:1 to 16:1.

22. The invention as described in claim 14, wherein the sleeve is affixed to the proximal connector means and the distal connector means by means of an adhesive.

23. The invention as described in claim 14 wherein the sleeve is affixed to the rotatable bearing means by mechanical connection means which are selectively releasable by a user of the apparatus such that a user may remove and replace sleeves at will, so as to allow selective installation of sleeves of varying resistance.

24. The device as described in claim 14, wherein the bearing means includes a plurality of rotating bearings.

25. The device as described in claim 14, wherein the sleeve and bearing means are configured to retain the bulge formed in the sleeve while the appendage is in a natural, undeflected configuration.

26. The device as described in claim 14, wherein the sleeve and bearing means are constrained to pivotal motion about the axis of rotation.

27. A device configured for joining a prosthetic appendage to a prosthetic limb, comprising:
   rotatable bearing means having a proximal portion, a distal portion, and an axis of rotation, the proximal portion being configured to be affixed to an end of a prosthetic limb, and the distal portion being configured to be affixed to the appendage;
   a generally cylindrical sleeve of resilient material having a top portion, a bottom portion, a central portion, an inside surface, an outside surface, and a long axis, the sleeve being oriented to surround the bearing means with the long axis co-linear to the axis of rotation of the bearing means, the inside surface of the top portion of the sleeve being affixed to the proximal portion of the rotatable bearing means, the inside surface of the bottom portion of the sleeve being affixed to the distal portion of the rotatable bearing means, such that when the proximal and distal portions of the bearing means are rotated relative to each other, such rotation is resiliently resisted by torsional flexure of the central portion of the sleeve;
   a bulge, formed around the circumference in the central portion of the sleeve and directed away from the rotatable bearing means, such that the magnitude of torsional resistance provided by the central portion of the sleeve is modified;
   stress relief means, formed in the central portion of the sleeve, the stress relief means extending at least partially between the outside surface and the inside surface of the sleeve, and configured to reduce the resistance of the sleeve to torsional flexure;
   wherein the stress relief means includes a plurality of slits, formed in the sleeve, and oriented parallel to the long axis of the cylindrical sleeve.

28. A device configured for joining a prosthetic appendage to a prosthetic limb, comprising:
   rotatable bearing means having a proximal portion, a distal portion, and an axis of rotation, the proximal portion being configured to be affixed to an end of a prosthetic limb, and the distal portion being configured to be affixed to the appendage;
   a generally cylindrical sleeve of resilient material having a top portion, a bottom portion, a central portion, an inside surface, an outside surface, and a long axis, the sleeve being oriented to surround the bearing means with the long axis co-linear to the axis of rotation of the bearing means, the inside surface of the top portion of the sleeve being affixed to the proximal portion of the rotatable bearing means, the inside surface of the bottom portion of the sleeve being affixed to the distal portion of the rotatable bearing means, such that when the proximal and distal portions of the bearing means are rotated relative to each other, such rotation is resiliently resisted by torsional flexure of the central portion of the sleeve;
   a bulge, formed around the circumference in the central portion of the sleeve and directed away from the rotatable bearing means, such that the magnitude of torsional resistance provided by the central portion of the sleeve is modified;
   stress relief means, formed in the central portion of the sleeve, the stress relief means extending at least partially between the outside surface and the inside surface of the sleeve, and configured to reduce the resistance of the sleeve to torsional flexure;
   wherein the stress relief means includes a plurality of slits, formed in the sleeve, and extending from the outside surface to the inside surface of the sleeve.

29. A device configured for joining a prosthetic appendage to a prosthetic limb, comprising:
   a proximal connector having a top configured to be affixed to the limb, and a bottom;
   a distal connector having a top generally opposing the bottom of the proximal connector, and a bottom configured to be affixed to the appendage;

rotatable bearing means, disposed between the bottom of the proximal connector and the top of the distal connector, for rotatably connecting the proximal and distal connectors relative to each other about an axis of rotation configured to be substantially parallel to a long axis of the limb;

a generally cylindrical sleeve of resilient material, surrounding the bearing means, having a top portion affixed to the proximal connector, and a bottom portion affixed to the distal connector to resiliently resist rotation between the proximal and distal connectors by torsional flexure of the sleeve;

a bulge, formed around a circumference of the sleeve and directed away from the axis of rotation, to provide additional unfixed sleeve material to reduce the magnitude of torsional resistance provided by the sleeve.

30. The device as described in claim 29, wherein the bearing means is constrained to pivotal motion about the axis of rotation.

31. The device as described in claim 29, wherein the bearing means includes a plurality of rotating bearings.

32. The device as described in claim 29, wherein the sleeve and bearing means are configured to retain the bulge formed in the sleeve while the appendage is in a natural, undeflected configuration.

* * * * *